(12) United States Patent
Coehoorn et al.

(10) Patent No.: US 7,048,890 B2
(45) Date of Patent: May 23, 2006

(54) SENSOR AND METHOD FOR MEASURING THE AREAL DENSITY OF MAGNETIC NANOPARTICLES ON A MICRO-ARRAY

(75) Inventors: Reinder Coehoorn, Eindhoven (NL); Menno Willem Jose Prins, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/498,958

(22) PCT Filed: Dec. 17, 2002

(86) PCT No.: PCT/IB02/05567

§ 371 (c)(1),
(2), (4) Date: Jun. 16, 2004

(87) PCT Pub. No.: WO03/054523

PCT Pub. Date: Jul. 3, 2003

(65) Prior Publication Data

US 2005/0087000 A1    Apr. 28, 2005

(30) Foreign Application Priority Data

Dec. 21, 2001    (EP) .................... 01205152

(51) Int. Cl.
*G01N 27/06* (2006.01)
*G01N 27/02* (2006.01)
*G01N 27/12* (2006.01)

(52) U.S. Cl. .............. 422/82.02; 422/50; 422/68.1; 422/82.01; 435/6; 435/7.1; 435/287.1; 435/287.2; 435/287.9; 435/288.3; 435/288.4; 436/524; 436/525; 436/526; 210/222

(58) Field of Classification Search .............. 435/4, 435/6, 7.1, 7.4, 283.1, 285.2, 287.1, 287.2, 435/288.3, 514, 518; 436/514, 518, 526; 422/68.1, 82.02; 428/692, 694
See application file for complete search history.

(56) References Cited

U.S. PATENT DOCUMENTS

| | | | | |
|---|---|---|---|---|
| 5,021,736 A | * | 6/1991 | Gonsalves et al. | 324/202 |
| 5,411,814 A | * | 5/1995 | Jin et al. | 428/692 |
| 5,412,087 A | * | 5/1995 | McGall et al. | 536/24.3 |
| 5,447,781 A | * | 9/1995 | Kano et al. | 428/212 |

(Continued)

FOREIGN PATENT DOCUMENTS

WO    WO 200114591 A1 * 3/2001

OTHER PUBLICATIONS

Baibich, M.N. et al., "Giant magnetoresistance of (001)Fe/(001)Cr magnetic superlattices", 1988, Physical Review Letters, vol. 61, pp. 2472-2475.*

(Continued)

*Primary Examiner*—Long V. Le
*Assistant Examiner*—Unsu Jung

(57) ABSTRACT

Method and device for magnetic detection of binding of biological molecules on a biochip in which a magnetoresistive sensor device measures an areal density of magnetic nanoparticles on a micro-array, the magnetic nanoparticles being directly or indirectly coupled to a target sample. The magnetoresistive sensor device includes a substrate having attached thereto binding sites able to selectively bind the target sample, and a magnetoresistive sensor for detecting the magnetic field of the nanoparticles coupled to the target sample. The magnetoresistive sensor includes a plurality of magnetoresistive sensing elements, the width and length dimensions of which are at least a factor 10 or more, preferably a factor 100 or more larger than the diameter of the nanoparticles.

35 Claims, 10 Drawing Sheets

U.S. PATENT DOCUMENTS

| | | | | |
|---|---|---|---|---|
| 5,569,544 | A | * | 10/1996 | Daughton .................... 428/611 |
| 5,739,990 | A | * | 4/1998 | Ravipati et al. ........ 360/324.12 |
| 5,981,297 | A | * | 11/1999 | Baselt .......................... 436/514 |
| 6,592,820 | B1 | * | 7/2003 | Hardman et al. .............. 422/65 |
| 6,844,202 | B1 | * | 1/2005 | Prinz et al. .................. 436/526 |
| 2002/0119470 | A1 | * | 8/2002 | Nerenberg et al. .............. 435/6 |
| 2004/0033627 | A1 | * | 2/2004 | Aytur et al. .................. 436/526 |
| 2004/0219695 | A1 | * | 11/2004 | Fox ............................. 436/526 |

OTHER PUBLICATIONS

Baselt, D.R. et al. "A biosensor based on magnetoresistance technology", 1998, Biosensors & Bioelectronics, vol. 13, pp. 731-739.*

Edelstein, R.L. et al. "The BARC biosensor applied to the detection of biological warfare agents", 2000, Biosensors & Bioelectronics, vol. 14, pp. 805-813.*

Schotter, J. et al. "Comparison of a prototype magnetoresistive biosensor to standard fluorescent DNA detection", 2004, Biosensor & Bioelectronics, vol. 19, pp. 1149-1156.*

Smith, N. et al., "A high-sensitivity magnetoresistive magnetometer", 1991, Journal of Applied Physics, vol. 69, pp. 5082-5084.*

Vassiliou, J.K. et al., "Magnetic and optical properties of gama-Fe2O3 nanocrystals", 1993, Journal of Applied Physics, vol. 73, pp. 5109-5116.*

* cited by examiner

SENSOR AND METHOD FOR MEASURING THE AREAL DENSITY OF MAGNETIC NANOPARTICLES ON A MICRO-ARRAY

This application is a National Stage application under 35 U.S.C. §371 and claims benefit under 35 U.S.C. §119(a) of International Application No. PCT/IB02/05567 having an International Filing Date of Dec. 17, 2002, which claims benefit of EP 01205152.0 filed on Dec. 21, 2001.

The present invention relates to a method and apparatus for sensing of randomly positioned nanometer-scale magnetic particles. In particular it relates to magnetic detection apparatus and a method for binding of biological molecules on a micro-array or biochip.

The introduction of micro-arrays or biochips is revolutionising the analysis of DNA (desoxyribonucleic acid), RNA (ribonucleic acid) and proteins. Applications are e.g. human genotyping (e.g. in hospitals or by individual doctors or nurses), bacteriological screening, biological and pharmacological research.

Biochips, also called biosensor chips, biological microchips, gene-chips or DNA chips, consist in their simplest form of a substrate on which a large number of different probe molecules are attached, on well defined regions on the chip, to which molecules or molecule fragments that are to be analysed can bind if they are perfectly matched. For example, a fragment of a DNA molecule binds to one unique complementary DNA (c-DNA) molecular fragment. The occurrence of a binding reaction can be detected, e.g. by using fluorescent markers that are coupled to the molecules to be analysed. This provides the ability to analyse small amounts of a large number of different molecules or molecular fragments in parallel, in a short time. One biochip can hold assays for 1000 or more different molecular fragments. It is expected that the usefulness of information that can become available from the use of biochips will increase rapidly during the coming decade, as a result of projects such as the Human Genome Project, and follow-up studies on the functions of genes and proteins.

One method for electronically detecting binding of sample molecules to probe molecules has been demonstrated by Clinical Micro Sensors (CMS), a subsidiary of Motorola, and is described in D. H. Farkas, "Bioelectric detection of DNA and the automation of molecular diagnostics", The Journal of the Association for Laboratory Automation, volume 4, number 5 (1999), pp.20–24. They have developed a "bioelectric DNA detection chip". The principle requires the use of ferrocene label molecules, which are sources or sinks of electrons. Capture probes are attached to gold-coated electrodes on the biochip. Capture probes are single strands of DNA complementary to a unique region of the target DNA or RNA sequence. When a sample containing target DNA is introduced into the cartridge, specific capture probes on an electrode surface encounter complementary DNA from the sample. Then binding, or hybridisation, occurs. The system also contains DNA sequences, called signaling probes, with proprietary electronic labels attached to them. These signaling probes also bind to the target DNA sequence. Binding of the target sequence to both the capture probe and the signaling probe connects the electronic labels to the surface. Binding of a molecular fragment is detected by the occurrence of an AC current through an electrode on which the molecules are bound, when a slight AC voltage is applied between the electrode and the solution above the chip, because the labels release electrons, producing a characteristic signal that can be detected through the electrode. This indicates the presence of the target DNA. Within this concept, the signal is proportional to the absolute number of binding reactions that have taken place. The number of electrons that flow, per cycle, and per bound DNA/c-DNA pair, is very small (a few, or a few tens). The above-mentioned paper mentions that in practice currents are in the pA to µA range, unfortunately without specifying the electrode area or the absolute number of bound pairs (presumably very large numbers). Proprietary signal processing technology is used to identify and quantify the target DNA sequence.

A second principle is a Bead Array Counter (BARC) biochip, as described in D. R. Baselt, "A biosensor based on magnetoresistance technology", Biosensors & Bioelectronics 13, 731–739 (1998); in R. L. Edelstein et al., "The BARC biosensor applied to the detection of biological warfare agents", Biosensors & Bioelectronics 14, 805 (2000); and in M. M. Miller et al., "A DNA array sensor utilizing magnetic microbeads and magnetoelectronic detection", Journal of Magnetism and Magnetic Materials 225 (2001), pp.138–144.

Using magnetoresistive materials, a rugged, single-component, micro-fabricated detector is produced, that will simultaneously monitor hundreds, thousands or even millions of experiments. As shown in FIG. 1, the detector 100 has an array of many micron-sized magnetoresistive sensors 101. For clarity, only two probe sites, each with one GMR sensor, are shown. These sensors 101 are located at a very small depth (=thickness of the silicon nitride $Si_3N_4$ passivation layer 102 combined with that of a relatively thin gold layer 103) below the surface of the substrate to which two probe DNA 104 is attached. Biotinylated sample DNA 105 binds to the probe DNA 104, if the nucleotide sequences the pairs formed are complementary. To the solution, microbeads 106 coated with free-floating magnetic streptavidin 107 are added, after probe-sample DNA hybridization has taken place. The beads 106 bind to the sample DNA that has hybridized with probe DNA 104 by the formation of a streptavidin-biotinyl bond. So if sample DNA 105 having sequences complementary to both probes 104 is present, the sample DNA 105 will attach the beads 106 to the sensors 101. The beads 106 used have a diameter of the order of 1 µm. In the beads 106, nanometer scale magnetic particles are present (not represented in the drawing), which are superparamagnetic due to their small size. Those nanometer-sized particles are typically of iron oxide, and are dispersed in, layered onto, or coated with a polymer or silica matrix to form beads of about 1 µm in diameter. Non-binding beads are taken away by making use of a small magnetic field in combination with a small field gradient or by rinsing with a buffer solution. The presence of the binding beads on the biochip is then detected by magnetising the particles in a relatively small, known, external magnetic field that is directed perpendicular to the plane of the substrate.

Although the example given above is for detection of DNA, also other molecules such as e.g. proteins can be detected by means of the prior art BARC biochip.

In the above-mentioned articles, the presence of particles is detected by making use of giant magnetoresistive (GMR) half Wheatstone bridge type sensors in the substrate, with a resistance versus applied field curve as shown in FIG. 2. The half Wheatstone bridge consists of one sensitive part above which beads are present, and one reference part above which no beads are present. The resistance versus field curve of the GMR material used is almost symmetric around zero field, as shown in FIG. 2, so that the sign of the field direction is not measured. The resistance of the GMR material decreases by about the same amount in response to a positive or negative applied field. It can be seen from FIG. 2 that there is a certain hysteresis in the GMR material, which is particularly manifest close to zero field. Consequently, accurate detection of small magnetic fields is almost impossible.

The BARC biochipconcept works, but the results given in FIG. 9 of D. R. Baselt, "A biosensor based on magnetoresistance technology", Biosensors & Bioelectronics 13, 731–739 (1998) show a poor signal-to-noise ratio(SNR). The main problem is that the large (1 µm scale) beads used diffuse slowly through the solution, so even after a relatively long time allowed for binding between the beads and the sample DNA only a relatively small number of beads will have bound to hybridized sample molecules, leading to a weak signal. Secondly, the beads have a certain distribution of their magnetic moment (at a given field), which negatively affects the signal-to-noise ratio when only one or a few beads are present per sensor. As shown by the authors, the signal-to-noise ratio for measurement of a single bead could be enhanced by making use of smaller sensor surface areas. However, when many sensors per probe are used the electronic circuitry that is required becomes very complex. Furthermore, the slow Brownian motion of the large magnetic particles of about 1 µm means that it can take a long time before the magnetic particle reaches a binding site. Thus actual measurements take a long time.

Tondra et al. describe in "Model for detection of immobilized superparamagnetic nanosphere assay labels using giant magnetoresistive sensors", J. Vac. Sci. Technol. A 18(4), July/August 2000, pp.1125–1129, that a GMR sensor can detect a single paramagnetic bead of any size, as long as a certain conditions are met, one of which is that the sensor is about the same size as the bead. This condition is easily met at a bead radius of 500 nm. Reducing the bead radius to 100 nm is possible by overcoming technical difficulties in fabrication of GMR sensors. Reducing the bead radius further to 10 nm is said to require advances in bead fabrication technology as well as in GMR sensor fabrication. A disadvantage of this solution is the required precise positioning of the probe areas with respect to the GMR sensor, on a scale well below 0.5 µm.

Chemla et al. describe in the article "Ultrasensitive magnetic biosensor for homogeneous immunoassay", PNAS, Dec. 19, 2000, vol. 97, no. 26, a SQUID based sensor using magnetic nanoparticles. An in-plane magnetic field is applied to de-randomise the magnetic moments of the magnetic nanoparticles attached to an immobilised zone on a substrate. The immobilised zone lies in a well and a MYLAR® sheet is described as an example thereof. Then, the field is switched off. The relaxation of the magnetic dipoles of the attached nanoparticles according to the Néel mechanism produces a measurable time dependence of the magnetic flux through the SQUID for a period of several seconds. This flux is detected by a SQUID probe placed close to the edge of the immobilised zone. Superparamagnetic nanoparticles in the bulk liquid are free to move according to Brownian motion and produce, in the absence of an applied field, no magnetic field. SQUID flux detectors have the disadvantage that they are expensive and that they operate only at cryogenic temperatures.

It is an object of the present invention to provide a method and device for accurate detection of magnetic particles in biochips with an enhanced signal to noise ratio.

It is another object of the present invention to provide a fast method for detection of magnetic particles in biochips and a corresponding device.

It is still another object of the present invention to provide a method and device for detection of magnetic particles, which are simple and economical, and in particular which do not require a precise positioning of individual magnetic beads with regard to the sensors.

The above objectives are accomplished, according to the present invention, by a magnetoresistive sensor device for determining the presence or an areal density of magnetic nanoparticles being directly or indirectly coupled to the target, the magnetoresistive sensor device comprising a substrate having attached thereto a binding site able to selectively bind a target, and a magnetoresistive sensor for detecting the magnetic field of magnetic nanoparticles at least when coupled to the target, wherein the magnetoresistive sensor comprises pairs of first and second magnetoresistive sensing elements or first and second groups of magnetoresistive sensing elements, each pair being associated with and located parallel with a probe element having at least one binding site, the outputs of the first and second magnetoresistive elements or first and second groups of magnetoresistive sensing elements being fed to a comparator circuit.

The present invention also includes a method for determining the presence or for measuring an areal density of magnetic nanoparticles on a substrate, comprising the steps of:

binding a target to selective binding sites on the substrate, the target being directly or indirectly labeled with magnetic nanoparticles, sensing the presence of the bound magnetic nanoparticles to a binding site to thereby determine the presence or density of the target labeled with magnetic nanoparticles wherein the sensing step is carried out by extracting two signals derived from the magnetic field generated by nanoparticles bound to the one binding site using magnetoresistive sensor elements; and determining the difference between the two signals.

The width and length dimensions of the probe areas, that are the areas on the chip at which the probe elements such as antibodies are attached, and of the magneto-resistive (MR) sensor elements, are much larger than the diameter of the magnetic nanoparticles of which the presence and concentration is to be measured. The nanoparticles may for example have a diameter between 1 and 250 nm, preferably between 3 and 100 nm, most preferred between 10 and 60 nm. For such small particles, the diffusion is fast. The width and length dimensions of sensor elements are at least a factor 10 or more, preferably a factor 100 or more, larger than the diameter of the nanoparticles, for example 1 µm×1 µm. Other dimensions for the sensor elements are also possible. If different dimensions are used, different S/N ratios are obtained.

The term "micro-array" or "biochip" refers to generated arrays on a planar surface that constitute a plurality of discrete reaction or incubation compartments identifiable by their locations or x-y coordinates on the array. Such arrays are suitable for use in assays for assessing specific binding characteristics between members of specific binding pairs. The invention is very suitable in competitive assays or displacement assays. These and other features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 12:
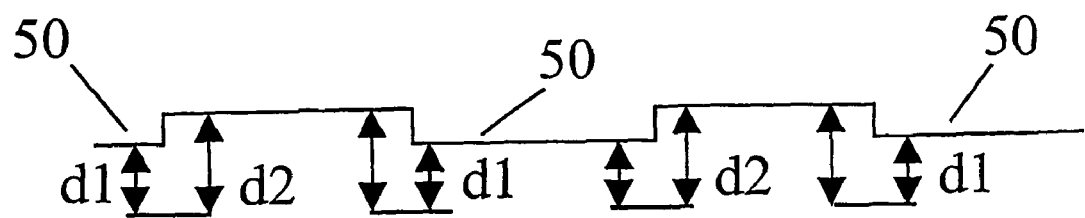

FIG. 12 schematically shows a multi-step structure above a plurality of magnetic sensor elements.

In the different drawings, the same reference figures refer to the same or analogous elements.

The present invention will be described with respect to particular embodiments and with reference to certain drawings but the invention is not limited thereto but only by the claims. For example, the present invention will be described with reference to two magnetoresistive sensor elements for each probe element but the present invention is not limited thereto. For example, 4, 6 or more even numbers of sensor elements may be used for each probe element and split into two groups. An output from each group is then transferred to a differential comparator or a summing circuit. The drawings described are only schematic and are non-limiting. The drawings are not drawn to scale.

The detailed description hereinafter gives a non-limiting example with the following specification:
a) the biochip area is 1×1 mm$^2$,
b) there are 100 different probes on the biochip area, each probe having an area (width $W_1$×length l) of $10^{-2}$ mm$^2$ (e.g. 100 μm×100 μm),
c) a measurement of the presence or absence of nanoparticles and/or nanoparticle density at each probe element is carried out 100 times during a total period of 3 minutes.

The present invention is not limited to such a system with the dimensions and values given, but is only limited by the claims.

Figure 1:
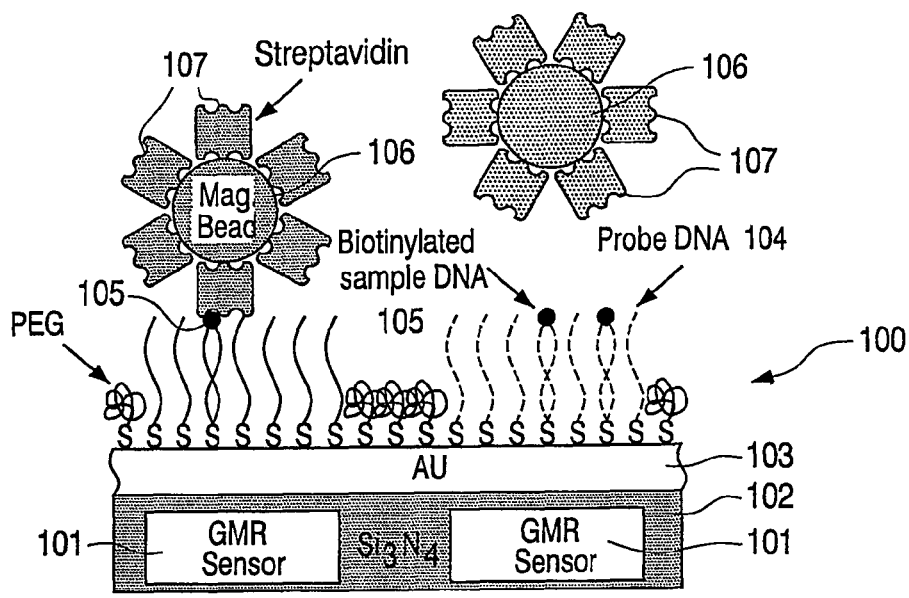
FIG. 1 is a schematic diagram of a BARC chip according to the prior art.
Figure 2:
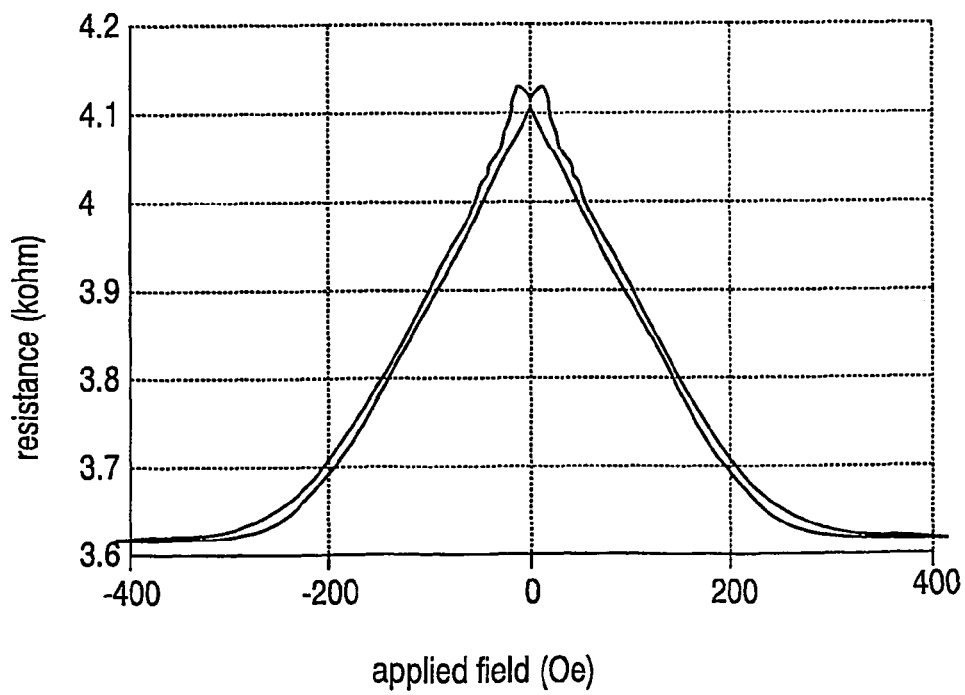
FIG. 2 is a graph of the response (resistance) of a multilayer GMR sensor device to an applied field according to the prior art.
Figure 3:
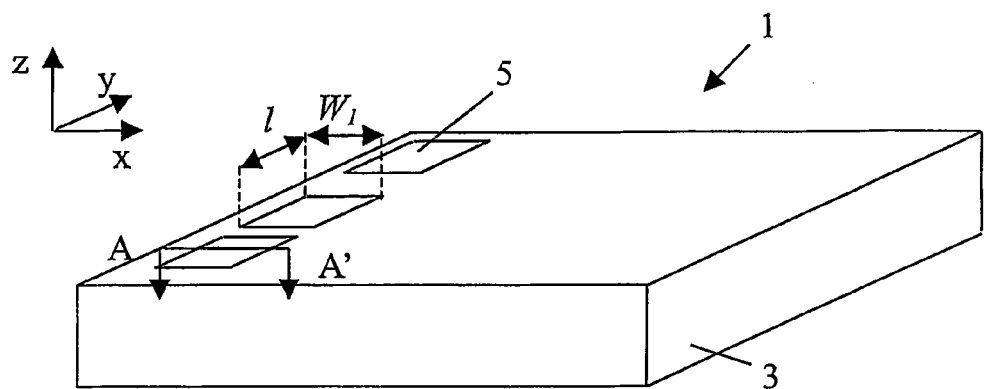
FIG. 3 is a perspective view of a biochip.

A biochip 1 comprises a substrate 3 with at its surface at least one, preferably a plurality of probe areas 5, as shown in FIG. 3. Each probe area 5 comprises a, preferably stripe shaped, probe element 7 over at least part of its surface, as shown in the two embodiments of FIG. 5A and FIG. 5B, which are explained below.

As shown in FIGS. 4A, 4B and 4C, 4D a probe element 7 is provided with binding sites 9, such as for example binding molecules or antibodies, able to selectively bind a target sample 11 such as for example a target molecule species or an antigen. Any biological molecule that can be coupled to a matrix is of potential use in this application.

Examples are:
Nucleic acids: DNA, RNA double or single stranded or DNA-RNA hybrids, with or without modifications. Nucleic acid arrays are well known.
Proteins or peptides, with or without modifications, e.g. antibodies, DNA or RNA binding proteins. Recently, grids with the complete proteome of yeast have been published.
Oligo- or polysaccharides or sugars
Small molecules, such as inhibitors, ligands, cross-linked as such to a matrix or via a spacer molecule The items spotted on the grid will be most likely libraries of compounds, such as peptide/protein libraries, oligonucleotides libraries, inhibitor libraries.

There exist different possibilities to connect magnetic nanoparticles 15 to the target 11, examples of which are shown in FIGS. 4A, 4B,4C and 4D.

Figure 4A:
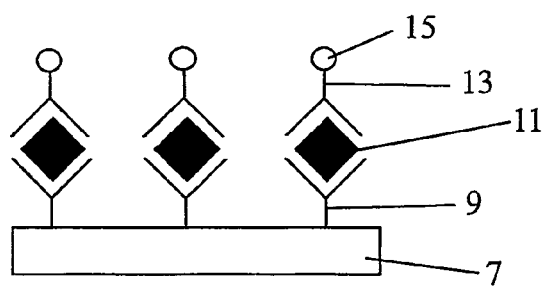
FIGS. 4A, 4B and 4C show details of a probe element provided with binding sites able to selectively bind target sample, and magnetic nanoparticles being directly or indirectly bound to the target sample in different ways.

In FIG. 4A, sensor molecules 13 labeled with magnetic particles 15 are able to selectively bind a target 11. When random searches are performed, e.g. screening which DNA binding proteins of a certain tissue extract bind to a grid with a library of nucleotides, the sensor molecule should have a very broad specificity. In this example a sensor molecule with a spacer reactive towards amino groups or carboxy groups would be useful. Other sensor molecules with a reactive group towards sugars, DNA are also suitable. In the case of a direct search, tailor-made sensor molecules can be used e.g. where a screening with a protein against a protein library is performed for assumed protein-protein interaction, an antibody is an obvious choice. Both monoclonal and polyclonal antibodies may be used. As shown in FIG. 4A, magnetic particles 15 are indirectly bound to the target sample 11.

Figure 4B:
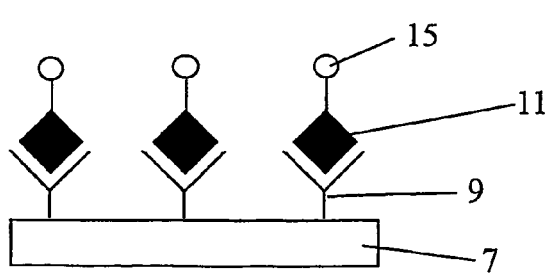

In FIG. 4B, the target sample 11 molecules are directly labeled by magnetic nanoparticles 15.

Figure 4C:
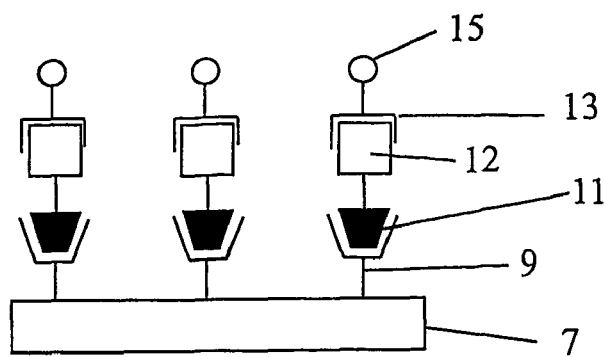

In FIG. 4C, target sample 11 is labeled by labels 12. Such a labeled target sample 11 (e.g. biotynilated sample DNA) is selectively bound to binding sites 9. Sensor molecules 13 (e.g. streptadivin) labeled with magnetic nanoparticles 15 are able to selectively bind the labels 12 on the target sample 11. Again, the magnetic nanoparticles 15 are indirectly bound to the target sample 11.

Figure 4D:
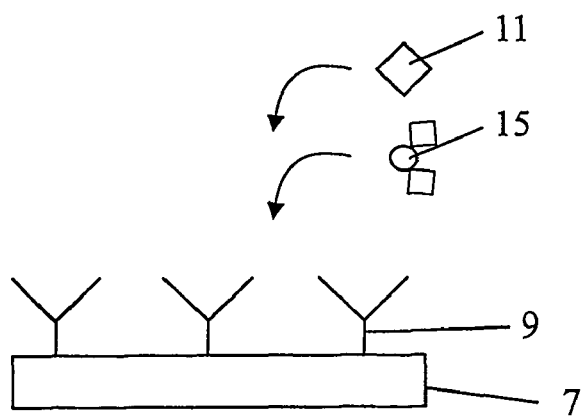
FIG. 4D shows a schematic of a competitive assay

In FIG. 4D, there is a target 11 and a target labeled with magnetic nanoparticles 15 present in the fluid or gas. In a competitive assay, the target with magnetic nanoparticles is able to selectively bind, if it reaches the binding site 9 earlier than the target reaches the binding site. The more target labeled with magnetic nanoparticles 15 has been bound, the less target was present in the fluid or gas.

According to the invention, the magnetic particles 15 are preferably superparamagnetic nanoparticles having a diameter less 1 μm, having an average magnetic moment m. With nanoparticles are meant particles having at least one dimension ranging between 1 nm and 250 nm, preferably between 3 nm and 100 nm, more preferred between 10 nm and 60 nm. They are attached to the probe element 7 on the substrate 3 of the biochip 1, either directly or indirectly, preferably by any of the methods illustrated in FIGS. 4A, 4B or 4C or similar. The nanoparticles 15 are usually positioned randomly within a well defined area on the chip 1, the well defined area being a probe area 5. The probe area 5 has a width $W_l$ and a length 1. The areal density of the nanoparticles 15 is n (nanoparticles per m$^2$). The areal density will in general be a function of time.

The probe area 5 can be a single long stripe. Instead of a single long stripe, also a certain number of shorter stripes next to each other can be used, so that the total area taken by a single probe 5 becomes squarer, more as shown in FIG. 3. As this does not affect the results on electronic sensitivity, only the case of a single long stripe shaped probe area 5 is further elaborated hereinafter.

The functioning of the biochip 1 is as follows. Each probe element 7 is provided with binding sites 9 of a certain type. Target sample 11 is presented to or passed over the probe element 7, and if the binding sites 9 and the target sample 11 match, they bind to each other. Subsequently, magnetic nanoparticles 15 are directly or indirectly coupled to the target sample 11, as illustrated in FIGS. 4A, 4B and 4C. The magnetic nanoparticles 15 allow to read out the information gathered by the biochip 1 The nanoparticles are preferably superparamagnetic nanoparticles 15 according to the present invention. Superparamagnetic particles are ferromagnetic particles of which at zero applied magnetic field the time-averaged magnetisation is zero due to thermally induced magnetic moment reversals that are frequent on the time scale of the magnetisation measurement. The average reversal frequency is given by $$v = v_0 \exp\frac{-KV}{kT}$$

where KV (with K the magnetic anisotropy energy density and V the particle volume) is the energy barrier that has to be overcome, and $v_0$ is the reversal attempt frequency (typical value: $10^9$ s$^{-1}$).

In some embodiments of the present invention the superparamagnetic particles 15 are preferably magnetised perpendicular to the plane of the chip in order to read out the information gathered by the biochip 1. In other embodiments the nanoparticles are magnetised parallel to the plane of the chip.

A magnetoresistive (MR) sensor, for example a giant magnetoresistive (GMR), a tunnel magnetoresistive (TMR) or an anisotropic magnetoresistive (AMR) sensor is provided according to the present invention to read out the information gathered by the biochip 1, thus to read out the presence or absence of the particles and/or to determine or estimate an areal density of the magnetic nanoparticles 15 on the probe area 5.

In an AMR, GMR or TMR material, the electrical resistance changes when the magnetization direction of one or more layers changes as a result of the application of a magnetic field. GMR is the magnetoresistance for layered structures with conductor interlayers in between the switching magnetic layers and TMR is the magneto-resistance for layered structures comprising magnetic metallic electrode layers and a dielectric interlayer.

In GMR technology, structures have been developed in which two very thin magnetic films are brought very close together. The first magnetic film is pinned, what means that its magnetic orientation is fixed, usually by holding it in close proximity to an exchange bias layer, a layer of antiferromagnetic material that fixes the first magnetic film's magnetic orientation. The second magnetic layer or free layer, has a free, variable magnetic orientation. Changes in the magnetic field, in the present case originating from changes in the magnetisation of the superparamagnetic particles 15, cause a rotation of the free magnetic layer's magnetic orientation, which in turn, increases or decreases resistance of the entire sensor structure. Low resistance generally occurs when the sensor and pinned layers are magnetically oriented in the same direction. Higher resistance occurs when the magnetic orientations of the sensor and pinned films oppose each other.

TMR can be observed in systems made of two ferromagnetic electrode layers separated by an isolating (tunnel) barrier. This barrier must be very thin, i.e., of the order of 1 nm. Only then, the electrons can tunnel through this barrier, an entirely quantum-mechanical transport process. Again, the magnetic alignment of one layer can be changed without affecting the other by making use of an exchange bias layer. Changes in the magnetic field, in the present case again originating from changes in the magnetisation of the superparamagnetic particles 15, cause a rotation of the sensor film's magnetic orientation, which in turn, increases or decreases resistance of the entire sensor structure.

The AMR of ferromagnetic materials is the dependence of the resistance on the angle the current makes with the magnetisation direction. This phenomenon is due to an asymmetry in the electron scattering cross section of ferromagnet materials.

In what follows, embodiments with a GMR sensor are considered but the present invention is not limited thereto.

Figure 5A:
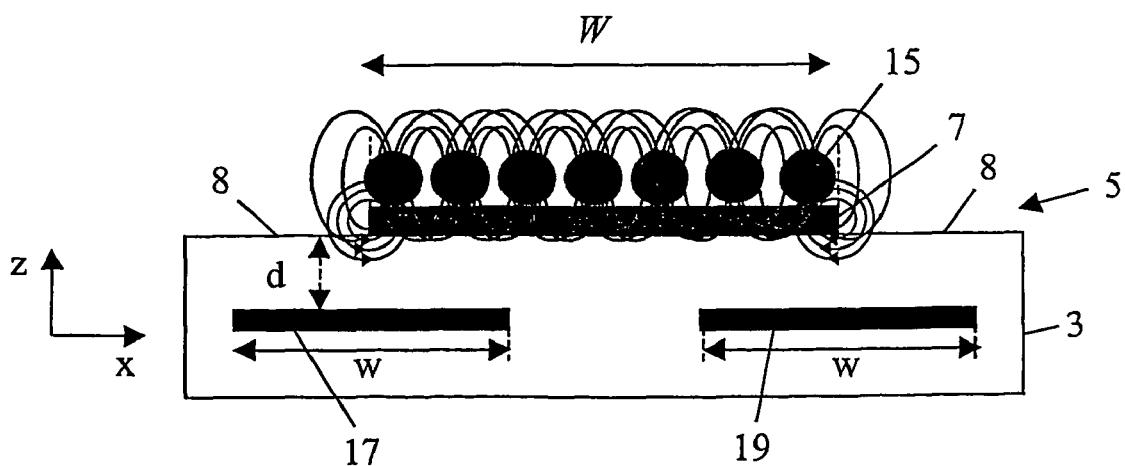
FIG. 5A is a cross-section of an embodiment of a probe area on the biochip of FIG. 3, according to A–A' in FIG. 3.
Figure 11:
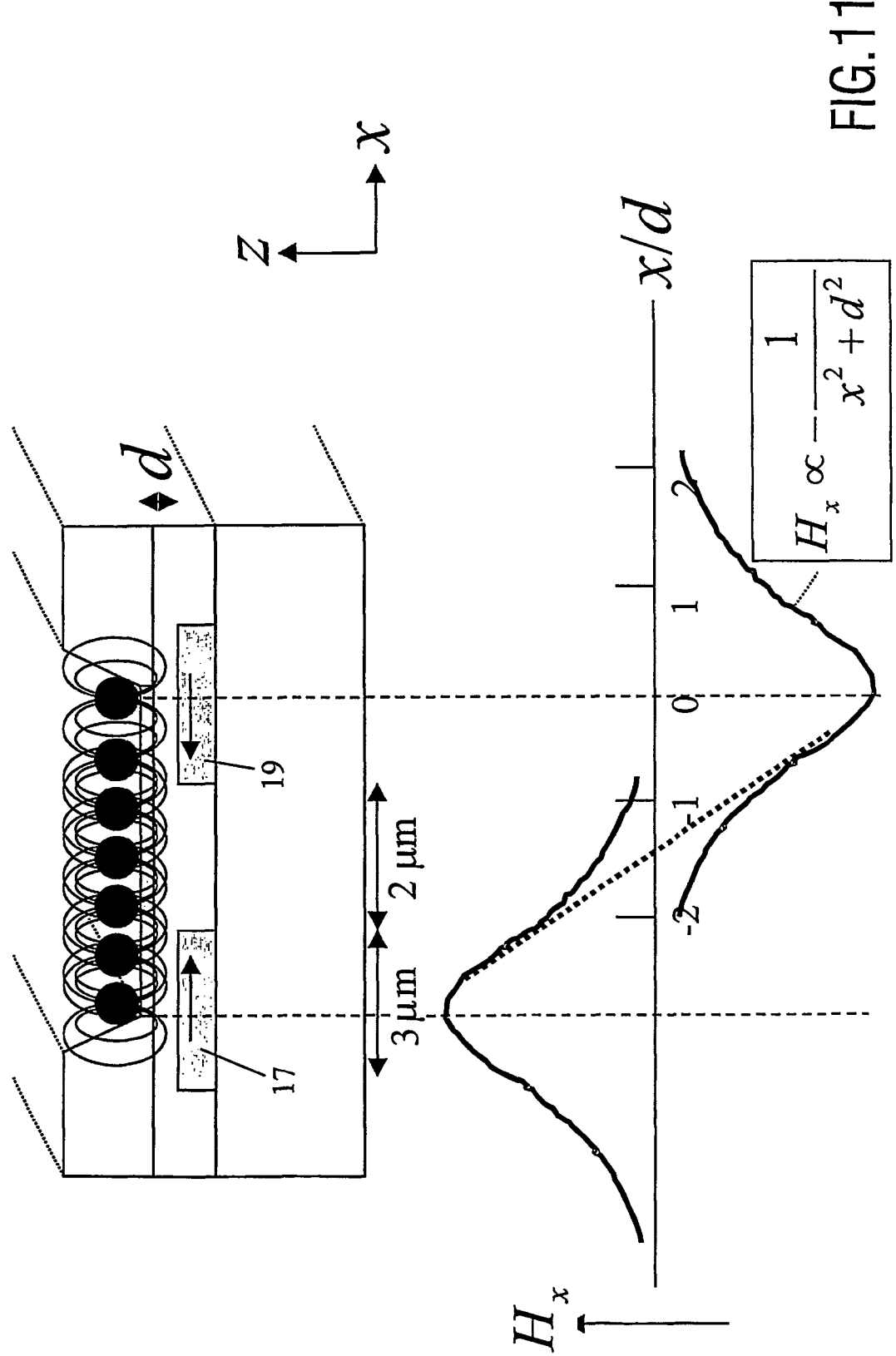
FIG. 11 is a graph illustrating the x-components of the magnetic field of the nanoparticles in the plane of the GMR sensor elements.

In a first embodiment, illustrated in FIG. 5A, the magnetoresistive sensor, e.g. a GMR sensor, comprises a first sensor element, e.g. a GMR element 17 and a second sensor element, e.g. a GMR element 19 integrated in the biochip substrate 3 at a distance d under the surface of the substrate 3. Each of those GMR elements 17, 19 comprises a pinned film with the same magnetisation direction, parallel or substantially parallel to the x-direction, and a free film or sensor film, the magnetisation direction of which is able to change due to an external magnetic field. In order to read out the biochip 1, the superparamagnetic nanoparticles 15 bound to it are magnetised by an external, uniform magnetic field perpendicular to the plane of the biochip 1. The use of the perpendicular magnetic field creates a net, average, magnetic field at the two sides of the stripe shaped area covered by the nanoparticles close to the sensor elements 17, 19. The probe areas overlap only with half of the GMR sensor stripes, so that the net average field in the sensor stripes created by the nanoparticles is largest along or near the central axis of the stripes. The magnetised nanoparticles 15 produce regions of opposite magnetic induction vectors in the plane of the underlying GMR films, as shown in FIG. 11, and the resulting magnetic field is detected by GMR sensor elements 17, 19. A co-ordinate system has been introduced in FIG. 3 and in FIGS. 5A and 5B, and according to that co-ordinate system, the probe element 7 and the GMR elements 17, 19 extend in the y direction over a length l. If the magnetoresistive sensor elements 17, 19 lie in the xy plane, the GMR sensor elements 17, 19 only detect the x-component of the magnetic field. The resulting magnetic field from the magnetised superparamagnetic particles 15 is detected by the first GMR element 17 and the second GMR element 19. Over the width W of probe element 7, the limited (non-infinite) spatial extent of the magnetic particles contributes to a net signal generated by the magnetic field in the plane of the GMR elements 17, 19. The magnetic particles at the edges of the probe element have no particles next to them on one side and therefore the magnetic field from these particles has a net in-plane field component in one direction within the sensor elements 17. 19. Particles which lie closer to the centre of a sensor 17, 19 will have their in-plane magnetic field neutralised to a certain extent by neighbouring particles on both sides. Thus all particles contribute to the signals generated in the sensor elements 17, 19. Although all nanoparticles make some contribution to the net field, the particles close to the probe element edges contribute more to the total magnetic field. Because a magnetic sensor element 17, 19 is most sensitive in the centre, the magnetic nanoparticles 15 at the edges of probe element 7 preferably are, in perpendicular projection, in the centre of the sensor elements 17, 19. The functioning of the sensor does not depend critically on the distance W between the GMR stripes, which can be chosen much larger than the diameter of the nanoparticles. As an example, the pinned films in the first GMR element 17 and the second GMR element 19 may both be oriented in the positive x-direction. In the example given in FIG. 5A, the magnetisation direction of the free film or sensor film of the first GMR element 17 will also be in the positive x-direction, and the magnetisation direction of the free films of the second GMR element 19 will be in the negative x-direction. The magnetisation directions of the pinned film and of the free film of the first GMR element 17 being the same, the first GMR element 17 exhibits a low resistance. As the magnetisation directions of the pinned film and of the free film of the second GMR element 19 are inverse, the second GMR element 19 exhibits a high resistance. The responses of the first GMR element 17 and the second GMR element 19 to the magnetic field present due to the magnetisation of the nanoparticles are shown in FIG. 5C (a) and (b) respectively. As shown in these graphs the magnetic field is either in the parallel or antiparallel direction compared with the biasing of the GMR element depending upon where the nanoparticle is placed.

Figure 6:
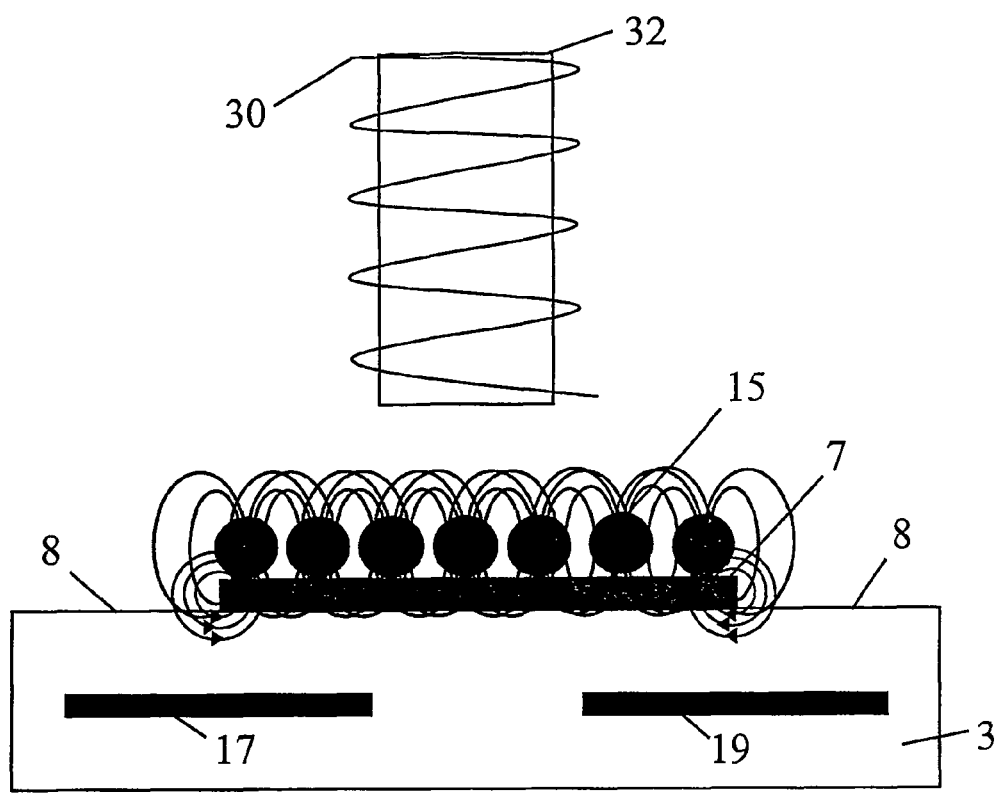
FIG. 6 illustrates a set-up in which two coils with a ferromagnetic core are used for magnetizing the magnetic nanoparticles.

The external magnetisation of the nanoparticles 15 can be done in any way known to a person skilled in the art. In particular it can be done by means of two coils 30 with a ferromagnetic core 32, as shown in FIG. 6. By applying a current of about 10 mA, for example, a magnetic field is generated, which is perpendicular to the substrate, in order to magnetise and align the magnetic moments of the nanoparticles 15. If the centres of both coils 30 are positioned along one line perpendicular to the substrate 3, if the coil diameter is approximately equal to or larger than the distance between the coils, and if the currents through the two coils are equal the magnetic field applied is to a good approximation perpendicular to the substrate 3 over an area equal to the coil area. It can be useful to create the option for varying the position of the coils such that a linear gradient of the magnetic field occurs at the probe area, by having a small (x,y,z) translation of one or both coils Alternatively, a gradient could be created by making use of a current difference. It can also be useful to create the option for slightly varying the orientation of the coils with respect to the sample area, resulting in small, well controlled in-plane field component. By making use of the combination of a magnetic field and a field gradient the strength of the binding of the magnetic particle can be determined in different directions. Bad binding can be detected, because at a certain magnetic field the magnetic nanoparticles lose their binding and are no longer detected by the MR sensor elements as they move into the bulk, too far from the sensors to be detected. This is of special importance to proteins that are large, while the binding of DNA is more ore less on/off. By making use of a small and well controllled in-plane field component in the x-direction, a correction can be made for a possible undesired shift of the center of the R(H) curves of the zero-field position, that in the case of exchange biased GMR or TMR sensors would result from a residual magnetic coupling between the free and pinned layers.

Figure 5B:
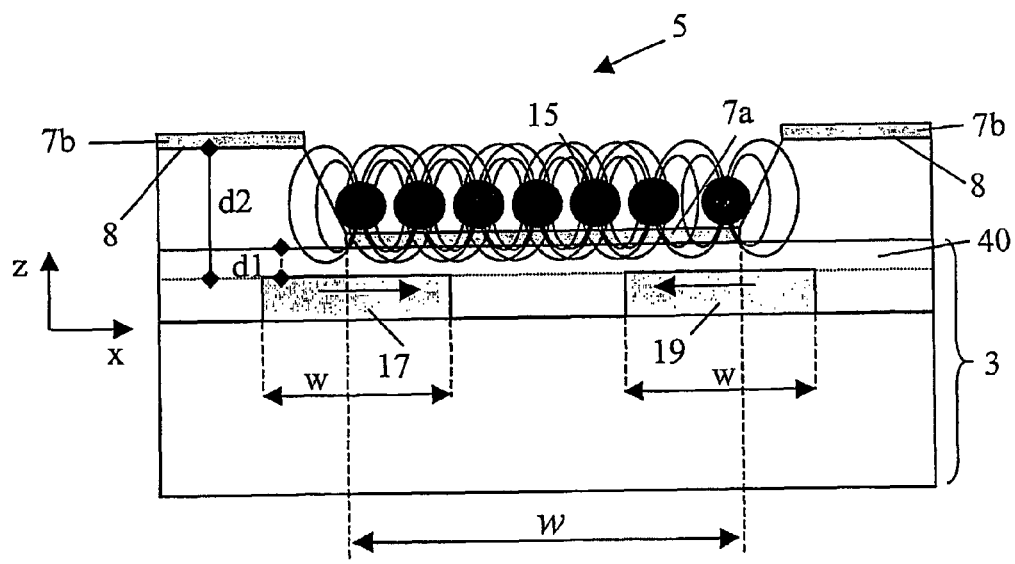
FIG. 5B is a cross-section of another embodiment of a probe area on the biochip of FIG. 3, according to A–A' in FIG. 3.
Figure 5C:
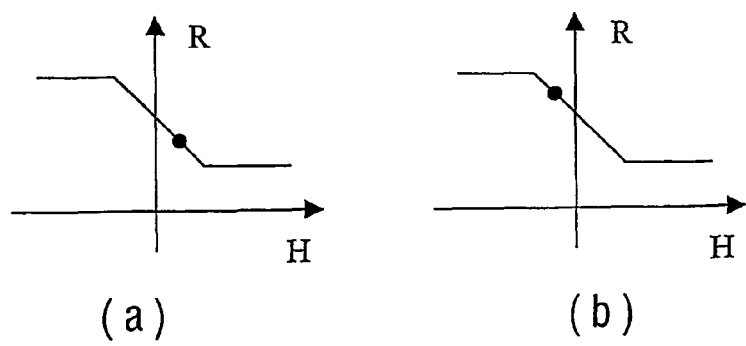
FIG. 5C is a graph of the response of a multilayer GMR sensor element to an applied field according to the present invention. The dots indicate schematically the punt R(H) values of each magnetoresistive sensor element wherein R is the resistance and H is the magnetic field.

In a second embodiment of a GMR sensor, illustrated in FIG. 5B, the surface of the probe area 5 has a buffer or isolation zone which prevents or reduces the effect of any nanoparticles accidentally in this zone from affecting the measurement. For example, the surface of the semiconductor sensor element can be structured. The purpose of the structuring can be to move the particles so far from the sensors that they no longer influence the measurement. Such structuring can be done physically, for example by means of a step profile or, as shown in FIG. 5B, with a gradient profile, e.g., by etching the semiconductor materials of the sensing element using anisotropic or isotropic etching solutions, e.g., to form a well, and thus a profiled surface. Alternatively, the probe area can be surrounded by a trench, deep enough to isolate any nanoparticles from the sensors. Besides or in addition to such a physical structuring, the surface of the probe area 5 can also be chemically or biochemically structured, e.g., by providing binding sites on probe element 7a of the probe area 5, but not on the regions 8 of the probe area 5 located next to the probe element 7b. Repellent materials may be used for these buffer zones. In FIG. 5B, sensor elements 17, 19 are arranged in the biochip substrate 3 at a distance d2 under the surface 8 on which probe element 7b is situated and in view of the formation of the well, are situated at a smaller distance d1 from the probe element 7a.

The sensor comprises thin film materials, in the example under reference GMR materials, but also other thin film materials such as AMR, TMR or other MR materials with substantially linear R(H) curves around H=0 are possible materials. The sensor is separated from the magnetic nanoparticles 15 by a separation layer 40, e.g. silicon dioxide, silicon nitride, or an organic material such as a resist or epoxy for example.

The magnetisation of the nanoparticles 15 is controlled by an external field applied perpendicular to the surface of the biochip 1 (i.e., along the z-axis). The sensor is now exposed to the magnetic field resulting from the nanoparticles 15, of which the (stripe-averaged) in-plane component is particularly high below the sides of the probe region covered with the magnetic nanoparticles. The change of the resistance difference of the sensors 17, 19, upon the application of a perpendicular magnetic field, is used to measure the areal density of nanoparticles on the probe element. The areal density of the magnetic nanoparticles 15 on the lower surface, probe element 7a, is given by density $\sigma_2$. The use of a recessed probe region ($d2 \neq 0$ in FIG. 5B) reduces the sensitivity to magnetic beads that reside on the surface at positions outside the probe area, i.e., without being specifically bound to probe molecules. In order to reduce the possible contribution to the signal of the volume density of nanoparticles in the fluid in the recessed region, an additional washing step can be applied, or particles can be pulled away from the sensor surface by the application of a magnetic field and a magnetic field gradient.

The areal particle density typically ranges between zero and $10^3$ to $10^4$ particles per $\mu m^2$.

In practice it is relatively easy to fabricate micrometer or sub-micrometer sized physical structures on surfaces, while it is much more difficult to fabricate high-quality biochemical surfaces with micrometer or submicrometer patterns.

Figure 7:
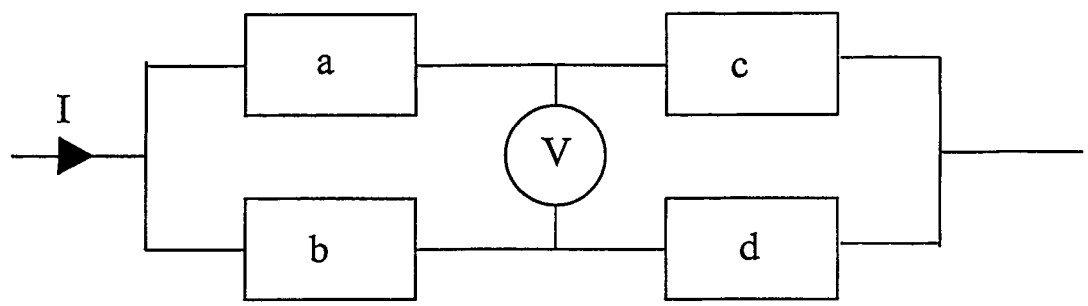
FIG. 7 is a schematic representation of a Wheatstone bridge.

In the second embodiment of the present invention, the sensor consists of a pair of sensor elements 17 and 19 in a configuration with respect to a probe area as shown in FIG. 5B. The areal density of magnetic nanobeads is derived from the difference of the resistance changes of the two sensor elements 17 and 19 upon the application of a perpendicular magnetic field. As sensor element 17 and 19 are equally sensitive to the effect of an in-plane component of the external field or due to thermal drift, these unwanted effects are cancelled. A practical method for obtaining the signal is to use sensors 17 and 19 as elements a and b in a Wheatstone bridge, as shown schematically in FIG. 7, in which the elements c and d are taken to be either (approximately) equal non-magnetic resistors, or magnetoresistors of the same type as sensors a and b, for which the resistance does not change in the applied field. This can be accomplished, e.g., by applying no probe molecules close to sensors c and d or by applying probe molecules above c and d sensors to a region that is much wider than the total width of the c and d sensor area (so that the net effect of all the dipolar fields is zero), or by locally applying a thick cover layer on top of sensors c and d so that the sensitivity to the presence of magnetic particles is strongly reduced. It is not necessary that the sensors c and d have the same physical dimensions as sensors a and b irrespective of the detailed practical method used for obtaining the signal we call such a system a half-Wheatstone bridge.

Figure 8:
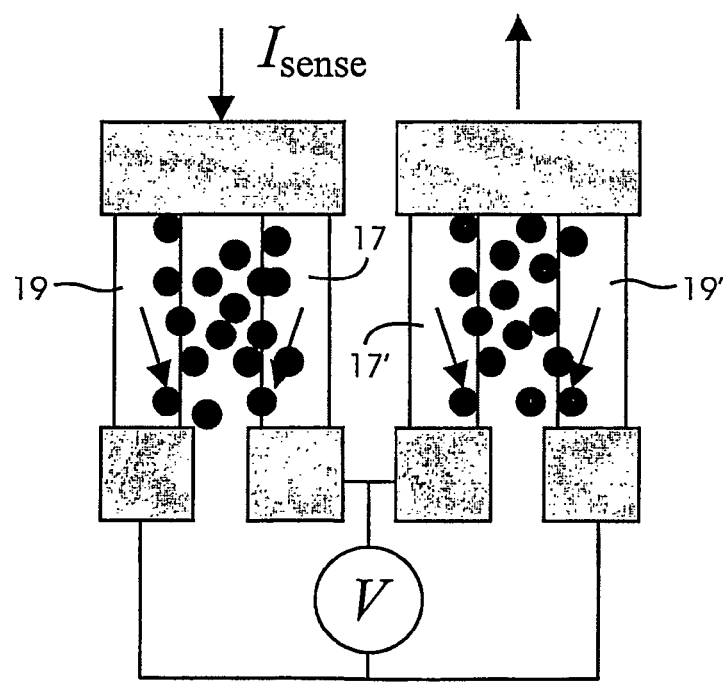
FIG. 8 is a schematic representation of a Wheatstone bridge configuration according to the present invention in which all parts are magnetically equal.

It is advantageous when the sensor elements 17 and 19 and nominally identical sensor elements 17' and 19' form a full Wheatstone bridge, as shown in FIG. 8. Here the elements 17, 19, 17' and 19' correspond to the elements a, b, d and c in the schematic structure shown in FIG. 7. For a fixed sense current $I_{sense}$, the signal from which the areal particle density is obtained from the voltage meter measured as shown in FIG. 8. A practical implementation of such a combination is schematically shown in FIG. 12, where a sequence of recessed regions 50 can be seen. The advantages of using differential measurements between two sensor elements 17, 19 for one probe element or between sets of sensors 17, 19 is that reference sensor elements are not required and a high detection sensitivity is obtained while maintaining independence from outside influences such as temperature. The sensitivity of a full Wheatstone bridge is twice the sensitivity of an otherwise identical half Wheatstone bridge.

The output of the comparator provides for example an indication of whether nanoparticles are present (when it exceeds a minimum threshold) or can be used to determine or estimate the areal density of the particles.

For stripe shaped GMR and TMR sensor materials comprising pinned and free magnetic layers, a substantially linear and hysteresis free resistance versus field curve can be obtained by making use of a magnetic configuration for which the exchange bias direction is perpendicular to the length direction (current direction), and for which the easy magnetization direction of the free layer is parallel to the length direction. The external field to which the sensor is sensitive is directed perpendicular to the stripe length direction. The field range ('switch field') in which the magnetization of the free layer rotates from a direction parallel to a direction antiparallel to the direction of the 'pinned' exchange biased layer is determined by the combination of various contributions to the magnetic anisotropy, including an intrinsic contribution that can, e.g., be due to growth in a magnetic field, and including the shape anisotropy. This is a so-called crossed anisotropy. In order to obtain a substantially linear R(H) curve around zero applied field, the effective magnetic coupling field that acts on the free layer due to the presence of the pinned layer should be reduced to a value well below the switch field. There are different contributions to this coupling. The coupling due to pinholes in the interlayer, the interlayer exchange coupling, and the magnetostatic coupling due to non-flat magnetic metal/interlayer interfaces can be reduced by making use of interlayers that are sufficiently thick. The magnetostatic coupling related to the finite stripe width can, e.g., be reduced by adapting the thicknesses of the free and pinned layer, or by making use of other that effectively reduce their magnetization times layer thickness product. It is also possible to not reduce these separate contributions to the coupling field, but to reduce the sum of all coupling contributions by designing a system in which the various contributions have opposite signs.

Well-known methods that lead to linear R(H) curves around zero field for AMR materials are the so-called soft-adjacent layer method and the barber-pole method. Both methods lead effectively to a configuration in which the angle between the current and the magnetization is close to 45° for H=0.

Figure 9A:
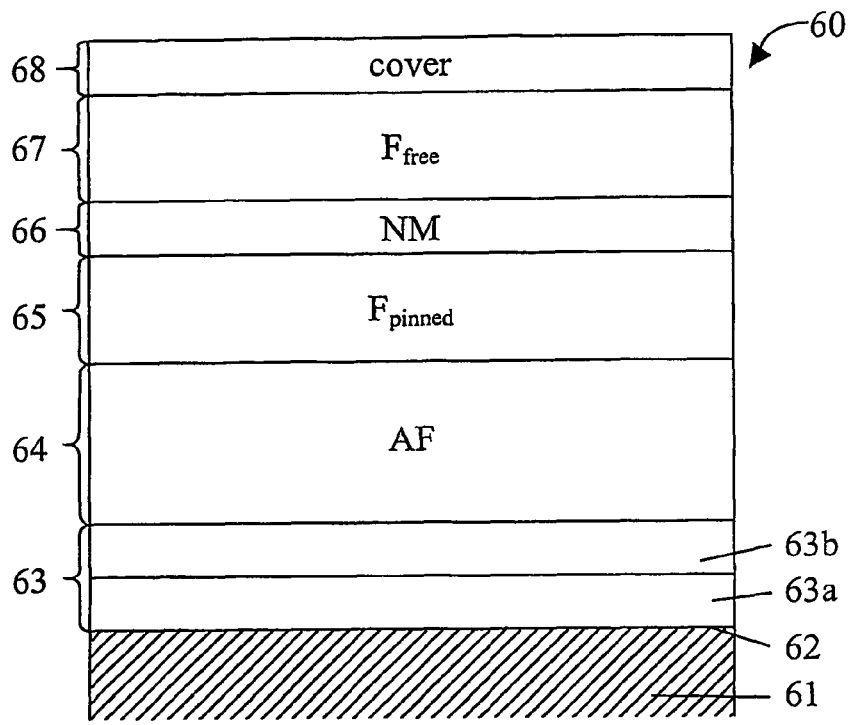
FIGS. 9A and 9B show a first and a second example respectively of suitable GMR structures for carrying out the present invention.

A first example of a suitable GMR structure 60 for a sensor device according to the present invention is as shown in FIG. 9A. The GMR structure 60 comprises a thermally oxidised Silicon substrate 61 having a major surface 62. On the major surface 62 of the substrate 61, a stack of layers is applied being first a (plurality of) buffer layer(s) 63, an antiferromagnet (AF) 64, a pinned ferromagnet ($F_{pinned}$) 65, a non-magnetic material (NM) 66, a free ferromagnet ($F_{free}$) 67 and a cover layer 68. 56, 66 and 67 are all metals. In particular, for this first example, each of the mentioned layers may consist of the following materials and thicknesses:

for the buffer layer 63: a 3 nm thick Ta layer 63a with on top thereof a 3 nm thick $Ni_{80}Fe_{20}$ layer 63b, for the AF 64: a 10 nm thick $Ir_{20}Mn_{80}$ layer, for the $F_{pinned}$ layer 65: a 6 nm thick Co layer, for the NM layer 66: a 3 nm Cu layer, for the $F_{free}$ layer 67: a 6 nm thick $Ni_{80}Fe_{20}$ layer, and for the cover layer 68: a 3 nm thick Ta layer.

The $Ir_{20}Mn_{80}$ layer 64 is an antiferromagnet (AF) which causes the magnetisation of the Co layer 65 to be pinned in a direction perpendicular to the length as of the GMR stripes 17, 19. This is done by growing the Co layer 65 in a magnetic field, or by cooling the system, after growing, in a magnetic field from a temperature above the so-called 'blocking temperature' (which is for the materials under consideration about 300° C.). The Cu layer 66 separates the pinned Co layer 65 from the free $Ni_{80}Fe_{20}$ layer 67. The upper Ta layer 68 protects the GMR structure 60 against oxidation when the wafer is exposed to air after deposition. The lower Ta layer 63a and the abutting $Ni_{80}Fe_{20}$ layer 63b aid in building or growing a suitable microstructure and crystal orientation.

Figure 9B:
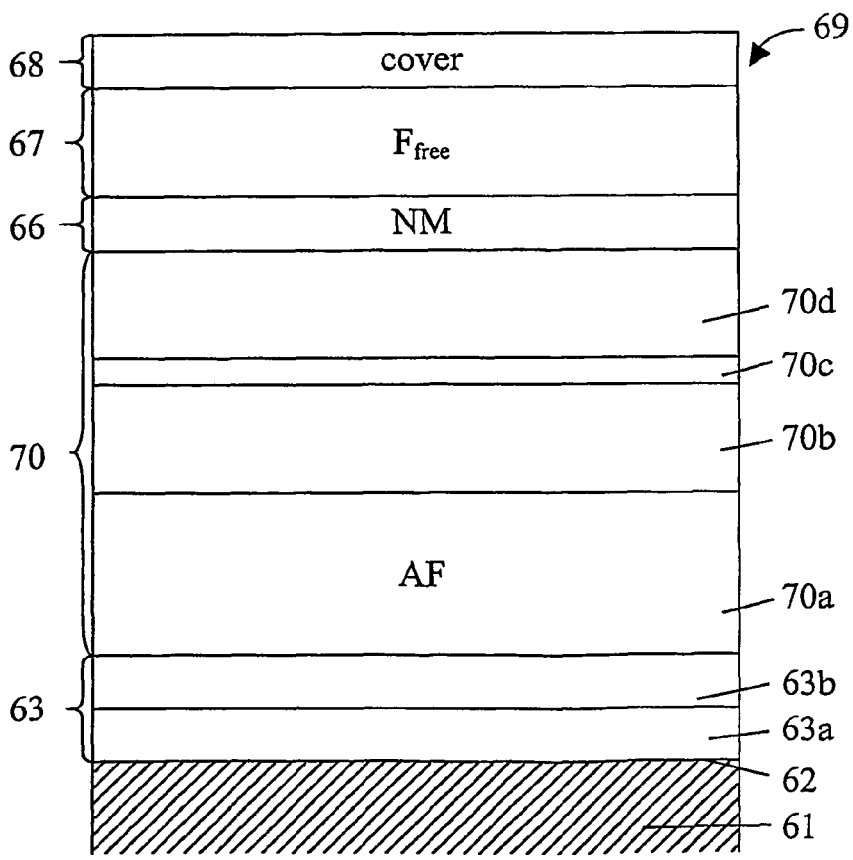

A second example of a suitable GMR structure 69 is shown in FIG. 9B. The GMR structure 69 comprises a thermally oxidised Silicon substrate 61 having a major surface 62. On the major surface 62 of the substrate 61, a stack of layers is applied being first a (plurality of) buffer layer(s) 63, then an artificial antiferromagnet (AAF) 70, a non-magnetic material (NM) 66, a free ferromagnet ($F_{free}$) 67 and a cover layer 68. In particular, for this second example, each of the mentioned layers may consist of the following materials and thicknesses:

for the buffer layer 63: a 3 nm thick Ta layer 63a with on top thereof a 3 nm thick $Ni_{80}Fe_{20}$ layer 63b, for the AAF 70: an AF layer, e.g. a 10 nm thick $Ir_{20}Mn_{80}$ layer 70a, a 6 nm thick Co layer 70b, a 0.8 nm Ru layer 70c and a 6 nm Co layer 70d, for the NM layer 66: a 3 nm Cu layer, for the $F_{free}$ layer 67: a 6 nm thick $Ni_{80}Fe_{20}$ layer, and for the cover layer 68: a 3 nm thick Ta layer.

The AAF layer 70 has the form of AF/Co/Ru/Co. The thickness of the Ru layer 70c is chosen so as to cause the magnetisation directions of the two Co layers 70b, 70d to be antiparallel due to exchange coupling over the Ru layer 70c. The AF layer 70a causes the magnetisations of the two Co layers 70b, 70d to be perpendicular to the length axis of the GMR stripes 17, 19.

This second GMR structure 69 has as advantage over the first GMR structure 60 that the magnetic structure is more stable with regard to external magnetic fields. Furthermore, due to the thickness ratio between the two Co layers 70b, 70d which are separated by the Ru layer 70c, an adjustable coupling between the pinned layer 70d and the free layer 67 can be chosen. This can compensate for a small coupling over the Cu layer 66 between the pinned layer 70d and the free layer 67. The sum of all couplings is chosen to be essentially zero, so that at zero applied field (no particles) the magnetisation of the free layer 67 is exactly perpendicular to the one of the pinned layer 70d (and thus parallel to the axis of the stripe 17, 19). The thinner the Cu layer 66, the larger the magnetoresistance, but also the larger the parallel coupling between the free and pinned layers 65 and 67 (or 70d and 67).(for thicknesses as from 3 nm). With the magnetostatic field from the AAF 70, of which the sign and size can be varied by varying by the difference of the thicknesses of the layers 70b and 70d, it is possible to correct for this, what leads to more sensitivity of the MR sensor device.

The diameter of the nanoparticles 15 (not shown in FIG. 3) is much smaller than W. With much smaller is meant at least a factor 10, preferably a factor 100 or more smaller.

There are three modes of operation, each of which is a separate embodiment of the present invention:

Measurement of the resistance change upon application of a magnetic field perpendicular to the plane of the sensor elements. Three possible embodiments have already given above: measurement by using a separate element, by differential comparison of the outputs of sensor elements 17, 19 (half Wheatstone bridge), or by using a full Wheatstone bridge (see above).

Measurement of the magnetisation after the magnetic field has been switched off. In this case, the field that is measured by sensor elements 17, 19 is due to the slow decay (thermal relaxation) of the magnetisation of those particles that are bound to the probe. The decay of the magnetisation from unbound particles is much faster, due to their fast random rotational motion. Soon after switching off the applied field, their net magnetisation is therefore negligible. Differential comparison detection (half and full Wheatstone bridge) can also be used in this mode.

Measurement of the magnetisation after an in-plane magnetic field has been switched off. This is a less preferred embodiment. In-plane magnetisation causes an in-plane magnetic field in the sensor elements 17, 19. This in-plane magnetic field is however, not as strong as the magnetic field close to the ends of the magnetic dipoles and therefore the sensitivity of this technique is lower. The magnetic field from the nanoparticles that is measured is also due to the slow decay (thermal relaxation) of the magnetisation of those particles that are bound to the probe. The decay of the magnetisation from unbound particles is also much faster, due to their fast random rotational motion. Soon after switching off the applied field, their net magnetisation is therefore negligible. However, in this mode the outputs from the two sensors 17, 19 are almost identical so that instead of using two sensors a single centrally placed sensor element may be used. In a half-Wheatstone bridge the resistance change of this sensor may be compared to that of a nominally identical (reference) sensor under an area on the chip at which no probe molecules, and hence no beads, are present. Similarly, a full Wheatstone bridge can be created by using a and d sensors that are situated below a probe region, and b and c sensors that are situated under an area on the chip at which there are no probe molecules.

In the present invention, all these modes are considered. In order to be able to provide all three modes with one device the sensor device may be equipped with means for generating either a magnetic field perpendicular to the plane of the probe element (modes 1 and 2) or a magnetic field parallel to the plane of the probe element in the plane of the nanoparticles (mode 3) or optionally both when desired. Similarly, switches may be provided to be able to measure the resistances of the sensor stripes separately, or e.g. to be able to measure sums or differences of resistances.

The required magnetic properties of the superparamagnetic particles 15, more specifically their relaxation time distribution, are different for the different modes, as discussed below.

The effect on the GMR signal due to the randomness of the positions of the nanoparticles 15 averages out when the probe element 7 is long enough in the y direction and the particle density n is large enough. A typical design may have a probe element 7 with length l=1 mm in the y direction, and with width W=3 in the x direction. The width w of each GMR element 17, 19 may be w=3 μm, of which about half in the x direction is located under the probe element 7. If the total width $W_t$ occupied by a probe area 5, is given by the width W of each probe element 7, half of the width of each of the two GMR elements 17, 19, plus a margin in order to eliminate cross-field effects, and that margin is taken 5 μm, there is sufficient space on a biochip 1 of 1×1 $mm^2$ for 100 probe areas 5 next to each other. The stripe-averaged field in case of a lot of particles per unit area, for nanoparticles 15 with magnetisation along the positive z-axis, is indicated schematically by the field lines in FIGS. 5A and 5B. It is equal to a magnetic field due to two parallel current wires at the edges of the stripes, with a current $$I = m \times n. \tag{eq. 1}$$

Obviously, the moments m per superparamagnetic particle 15 should be as large as possible for a given volume of the particle 15, in order to obtain a magnetic field which is as large as possible.

The GMR elements 17, 19 probe the x-component of the magnetic field, which is positive for the first GMR element 17 and negative for the second GMR element 19. If the origin of the coordinate system is taken in the middle of the first GMR element 17, then the average x-component of the field in that element 17 is $$H_{x,av} = \frac{1}{2\pi} \frac{1}{w} \int_{-w/2}^{w/2} dx \frac{m \times n \times d}{x^2 + d^2} = \frac{2}{2\pi} \frac{m \times n}{w} \times \arctan \frac{w}{2d} \quad \text{(eq. 2)}$$

Therefore $H_{x,av}$ can be increased by making the width w of the GMR elements 17, 19 small, and the depth d of the GMR elements 17, 19 under the substrate surface smaller than or approximately equal to w. Making the width W of the probe element 7 small does not change the field sensed at each of the GMR elements 17, 19, as long as the width W of the probe element 7 is approximately equal to the width w of the GMR elements 17, 19 and the depth d of the GMR elements 17, 19 under the substrate surface, or larger. The field due to the nanoparticles 15 on the middle of the probe element 7 is then not detected. Otherwise, the signal will decrease with decreasing width W of the probe element 7. So it is not usually advantageous to make the width W of the probe element 7 much larger than the width w of the GMR elements 17, 19, unless maybe for practical reasons such as patterning technology.

The pair of GMR elements 17, 19 in which the signal is opposite can be used to make a Wheatstone bridge configuration in which all parts are magnetically equal, that is in which there are equal exchange bias directions in all branches. An example of such a Wheatstone bridge is given in FIG. 8. The signal doubles, due to the elimination of a non-active reference MR element, and a common mode signal (e.g. due to in-plane external fields or due to thermal drift) is cancelled.

The signal voltage is given by:

$$V_S = 2 \times I_{sense} \times \Delta R = 2 \times I_{sense} \times \left(\frac{\Delta R}{R}\right)_{max} \times \frac{H_{x,av}}{\Delta H_{max}} \times \frac{l}{w} \times R_{sheet}, \quad \text{(eq. 3)}$$

wherein $I_{sense}$ is the sense current,
$R_{sheet}$ is the GMR sheet resistance, $$\left(\frac{\Delta R}{R}\right)_{max}$$

is the magnetoresistance ratio when the full dynamic range is used, and
$(\Delta H)_{max}$ is the field range in which the element switches completely. If shape anisotropy determines this range, $$(\Delta H)_{max} = 2 \times \frac{t}{w} M_{sat}, \quad \text{(eq. 4)}$$

where t and $M_{sat}$ are the thickness and saturation magnetisation of the free magnetic layer, respectively.

Combining (eq. 1)–(eq. 4) leads to:

$$V_S = \frac{1}{\pi} \times m \times n \times \arctan \frac{w}{2d} \times \left(\frac{\Delta R}{R}\right)_{max} \times \frac{I_{sense}}{t \times M_{sat}} \times \frac{l}{w} \times R_{sheet}$$

The electronic noise is assumed to be due to thermal noise. The r.m.s. thermal noise voltage is:

$$V_N = \sqrt{4kTR\Delta f} \cong \sqrt{4kT \frac{l}{w} R_{sheet} \frac{1}{t_{meas}}},$$

where the effective measurement time $t_{meas}$ is equal to the time during which the signal is measured, provided that just before the measurement the magnetisation can be assumed to be zero (because the particles are superparamagnetic). That defines a reference level. The signal to noise ration is equal to $SNR = V_S/V_N$.

For proper functioning of the system, for the first mode (measurement of the magnetisation during application of the field) it is preferred that the superparamagnetic relaxation time of all particles is much smaller, at least a factor 5 smaller, preferably a factor 10 or more smaller, than the period of time during which the field is applied and during which the measurement is carried out. The magnetisation of the particles is then switched on and off almost instantaneously upon switching the field on and off. In that case, the magnetic dipolar interaction between the particles after a measurement is negligible, and the binding reaction can proceed without being disturbed by such interactions in between the measurements. This requires that the magnetic particles in the nanobeads should have a product of the volume V and the magnetic anisotropy constant K that is sufficiently small. In this first mode of operation, the particles 15 that are not bound to the chip 1 should not be present at the chip interface during a measurement. This can be accomplished by a washing step just before each measurement, or by temporarily displacing the non-bound particles away from the chip 1 just after the application of a field plus a field gradient parallel to the normal direction. The resulting force should be sufficient for displacing the particles a few micrometers above the chip surface (where their dipolar field at the surface is small, and where their positions with respect to the GMR elements 17, 19 is sufficiently random, so that also for this reason the net signal is negligible). On the other hand, the force should be less than the force required for breaking a bond.

In the second (and third) modes of operation (measurement of the magnetisation after the field has been switched off), a field is first applied during a period $t_f$ and after switching off the field, p measurements of the decaying signal are carried out during a period $p \times t_{meas} \approx t_f$. Ideally, just after the magnetising field is switched off, all superparamagnetic particles 15 should be fully magnetised, but after the sequence of p measurements has been carried out, all particles 15 should have lost their magnetisation. Otherwise, the particles 15 would interact magnetically during the reaction periods in between measurement periods. This would imply that only particles 15 can be used for which the relaxation time is less than $t_f$. By the application of applied fields with alternating signs in successive measurement cycles, one can prevent that a small unwanted fraction of bound particles 15 with a relaxation time that is larger than $t_f$ builds up a total magnetic moment that increases monotonically with the number of completed measurement cycles, and that does not decay to zero in between the periods during which the field is applied. On the other hand, the relaxation time should be larger than $t_{meas}$ because otherwise even the first measurement after switching off the field would not yield a signal.

Practically, the above would imply that the relaxation time should be between 1 ms and 1 s (see below). This is a more difficult requirement than for the first mode of operation. Particles that fall outside this range do not contribute to the signal, and should ideally not be present. The particle diameter should therefore be to a very good approximation monodisperse. A method for creating such particles is known, and is described in S. Sun et al., "Monodisperse FePt Nanoparticles and Ferromagnetic Nanocrystal Superlattices", Science 287, 1989–1992 (2000).

The SNR is calculated for a system as specified by the table below, giving the system parameters for the example, for 35 nm commercially available magnetic particles, such as magnetite ($Fe_3O_4$) particles.

| | | |
|---|---|---|
| M | $1 \times 10^{-17}$ Am$^2$ | Magnetic moment of a spherical 35 nm magnetite particle (using the literature value of the room temperature magnetisation, M = 480 kA/m). |
| W | $3 \times 10^{-6}$ m | Width of probe element 7. |
| L | $1 \times 10^{-3}$ m | Length of probe element 7 and of GMR elements 17, 19. |
| W | $2 \times 10^{-6}$ m | Width of GMR elements 17, 19. |
| D | $0.5 \times 10^{-6}$ m | This allows a thick conducting layer in between the GMR element 17, 19 and the substrate surface, for the purpose of cooling. |
| $I_{sense}$ | 1 mA | Sense current; this value is not too large if a proper heat sink layer is used. |
| $\left(\frac{\Delta R}{R}\right)_{max}$ | 0.06 | Magnetoresistance ratio of the spin valve when the fall dynamic range is used |
| $R_{sheet}$ | 20 Ω | Sheet resistance of the spin valve |
| T | 3 nm | Layer thickness of the free magnetic layer of the spin valve |
| $M_{sat}$ | 800 kA/m | Saturation magnetisation of the free magnetic layer of the spin valve |
| T | 300 K | Room temperature |

The moment m indicated is the saturation moment, which is already obtained when the applied field is higher than 1.2 kA/m. The voltage over each MR element is 10 V. The power during a measurement, per probe, is 20 mW. The numerical results are as follows:

$$V_S = 8.8 \times 10^{-16} \times n \, [V]$$

$$V_N = 1.3 \times 10^{-8} \times \sqrt{\frac{1}{t_{meas}}} \, [V]$$

$$SNR = 6.8 \times 10^{-8} \times n \times \sqrt{t_{meas}}$$

If it is assumed that the minimum SNR required for the detection of the nanoparticles 15 is 10 (20 db), then the minimum detectable areal density of nanoparticles, $n_{min}$, is $$n_{min} \cong \frac{1.5 \times 10^8}{\sqrt{t_{meas}}} \, [particles/m^2]$$

The minimum number of detectable particles on a probe area of $10^{-8}$ m$^2$ (100 μm×100 μm) is $$\frac{1.5}{\sqrt{t_{meas}}}$$

The above theory breaks down if the absolute number of particles per probe area is too small. A lower limit may be 50. This implies that increasing the measurement time $t_{meas}$ will lead to a decrease of the minimum detectable number of nanoparticles, until $t_{meas}$ is of the order of 1 ms. Fortunately, this measurement time is well below the targeted repeat time of the measurements (100 measurements over 3 minutes). It is not useful to use a larger measurement time. It is therefore concluded that, for the parameters used, and when $t_{meas>}1$ ms, the minimum number of particles that can be measured with accuracy, 50 on a probe area, is determined by the statistics and not by the sensitivity of the GMR sensor.

The maximum measurable areal density of particles is equal to the lowest of the following two densities:

The density above which the magnetic dipolar interaction between the particles, or steric hindrance, becomes too strong. For 35 nm particles this may be at a density of the order of 100 particles per μm$^2$.

The density above which the field from the particles saturates the GMR sensor. In the continuum approximation used this happens if $H_{x,av}>\frac{1}{2}\Delta H_{sat}$, i.e. at a density of the order of approximately 960 particles per μm$^2$.

Neither of the two densities depends on the measurement time $t_{meas}$. In the case of the example given, the interparticle interaction, and not the GMR saturation field, will normally determine the maximum measurable number of particles.

The time averaged power dissipation is 2 mW for the first mode of operation, assuming 100 probes and a duty cycle of 1:1000 for each probe (one measurement per second, with a duration of 1 ms). Similarly, for the second mode of operation, the power dissipation is p×2 mW, where p is the number of 1 ms measurement intervals per cycle.

For the second mode of operation, 1/f noise may become important, especially if the period over which the decay of the signal is measured becomes as long as 1 s.

The above results can be generalised as follows. The areal density of particles that can be detected should not be below the density n_(stat) that corresponds to the statistically determined value of ≈50 particles per probe, below which the above theory breaks down. For probes with an area equal to $10^4$ μm$^2$, n_(stat)=0.005 μm$^2$. The areal density of particles that can be measured is certainly lower than the density n_+(int) at which interparticle interactions or steric hindrance become too large. It is assumed that n+(int)≈1.25× $10^5/d^2$, d being the particle diameter in nm. So, independent of the sensitivity of the GMR elements used, the measurement time and the magnetic moments of the particles, the highest possible width of the dynamic range is:

$$\text{max} \cdot \text{dynamic range} \approx \frac{2 \times 10^7}{d^2}.$$

From this point of view, the use of small particles is advantageous, as it increases the width of the dynamic range. However, the actual lower limit of the density may not be given by n_(stat), but by a value n_(sens)=$n_{min}$ that depends on the sensitivity of the GMR sensor. This is the case if n_(sens)>n_(stat). The value of n_(sens) is inversely proportional to the particle volume and to the squareroot of the measurement time. In addition, the actual upper limit of the density is not given by $n_+(int)$ but by the density $n_+(satur)$ at which the GMR element saturates, if $n_+(satur) < n_+(int)$. For the conditions assumed, $n_+(satur)=4.11 \times 10^7/d^3$.

Figure 10:
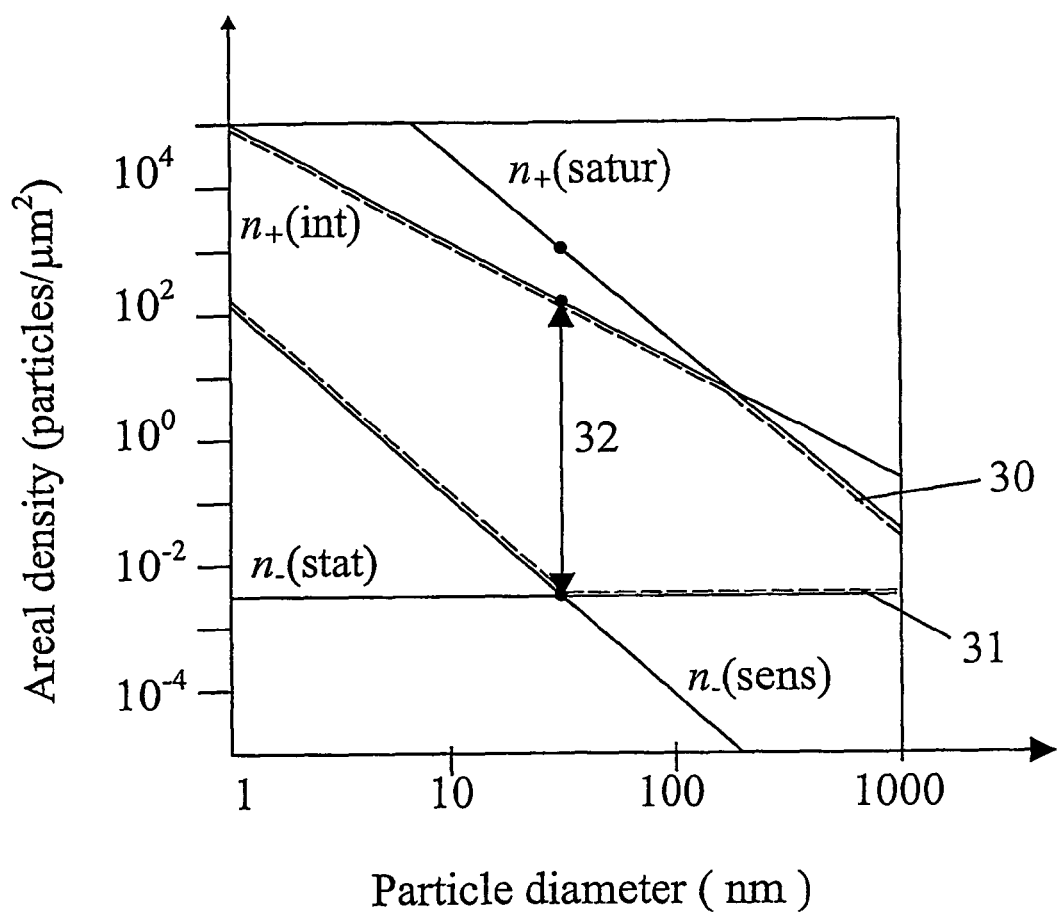
FIG. 10 is a graph showing upper and lower limits of the detectable areal density, as a function of the magnetic particle diameter

FIG. 10 is a graph showing areal density (in particles/$\mu m^2$) as a function of the particle diameter (in nm). From the diagram the dynamic range can be derived for the system considered, as a function of the magnetic particle diameter, for the parameter values given in the table above, and for a measurement time of 1 ms. The upper limits of the dynamic range are given for higher particle diameters by $n_+(satur)$, which is due to saturation of the magnetoresistive element, and for lower particle diameters by n+(int), which is due to interparticle interactions or steric hindrance. The lower limits of the dynamic range are given for higher particle diameters by $n_-(stat)$, which is due to the statistical (random) position of the particles on the probe area, and for lower particle diameters by $n_-(sens)$, which is due to sensitivity of the magnetoresistive element. The overall upper sensitivity limit is given by line 30, and the overall lower sensitivity limit is given by line 31. The dynamic range for 35 nm particles is given by the double arrow 32. It can be seen from FIG. 10 that, for the measurement time of 1 ms assumed, the particle radius of 35 nm is optimal. A decrease of the MR element saturation field or an increase of the particle magnetisation lead to parallel downward shifts of the $n_-(sens)$ and $n_+(satur)$ lines. Separately or in combination, these two improvements of the system could shift the optimal diameter to at best approximately 10 nm, leading to a dynamic range of $2 \times 10^5$.

It is to be remarked that it has been assumed for reasons of simplicity that the magnetising field will be able to fully magnetise the particles. For a maximum magnetising field of 115 kA/m, this assumption breaks down when the particle radius is below approximately 10 nm. The actual values of $n_-(sens)$ line are then higher than is indicated in FIG. 10.

While the invention has been shown and described with reference to preferred embodiments, it will be understood by those skilled in the art that various changes or modifications in form and detail may be made without departing from the scope and spirit of this invention.

The invention claimed is:

1. A magnetoresistive sensor device for determining a presence or an areal density of magnetic nanoparticles being directly or indirectly coupled to a target, the magnetoresistive sensor device comprising:
   a substrate;
   an elongate probe element arranged on the substrate and including at least one binding site able to selectively bind a target, the probe element having first and second opposite end regions defining a length therebetween and extending in a first direction; and
   a magnetoresistive sensor arranged in association with the probe element for detecting a magnetic field of magnetic nanoparticles at least when coupled to the target, wherein the magnetoresistive sensor comprises at least one pair of discrete, elongate first and second magnetoresistive sensing elements, each arranged only partially under the probe element, the first and second magnetoresistive elements each having a length and extending in the first direction such that the first and second magnetoresistive elements are parallel to the probe element, the first magnetoresistive element being arranged under the first end region of the probe element and the second magnetoresistive element being arranged under the second end region of the probe element such that the first and second magnetoresistive elements are separated and spaced apart from one another in the first direction,
   whereby outputs of the first and second magnetoresistive elements are fed to a comparator circuit which determines the presence or the areal density of magnetic nanoparticles coupled to the target bound to the at least one binding site of the probe element.

2. Magnetoresistive sensor device according to claim 1, further comprising means for generating a magnetic field perpendicular to the magnetoresistive sensing elements.

3. Magnetoresistive sensor device according to claim 1, wherein the substrate defines a probe area in which the probe element is arranged and there is an overlapping area between the magnetoresistive sensing elements and the probe area.

4. Magnetoresistive sensor device according to claim 3, wherein the first and second magnetoresistive sensing elements are arranged such that the probe area only partially overlaps with the first and second magnetoresistive sensing elements.

5. Magnetoresistive sensor device according to claim 3, wherein the probe area has a multi-level surface and a part of the probe element is arranged on each level, the probe element on a level closest to the first and second magnetoresistive sensing elements having the at least one binding site.

6. Magnetoresistive sensor device according to claim 1, further comprising means for generating a magnetic field parallel to the magnetoresistive sensing elements.

7. Magnetoresistive sensor device according to claim 1, wherein width and length dimensions of the first and second magnetoresistive sensing elements are at least a factor of 10 or more larger than the average diameter of the nanoparticles.

8. Magnetoresistive sensor device, according to claim 1, wherein the device is a microarray.

9. Magnetoresistive sensor device according to claim 1, wherein the first and second magnetoresistive sensing elements are giant magnetoresistive (GMR) elements.

10. Magnetoresistive sensor device according to claim 1, wherein the first and second magnetoresistive sensing elements are tunnel magnetoresistive (TMR) elements.

11. Magnetoresistive sensor device according to claim 1, wherein the first and second magnetoresistive sensing elements are anisotropic magnetoresistive (AMR) elements.

12. Magnetoresistive sensor device according to claim 1, wherein the first and second magnetoresistive sensing elements form a Wheatstone bridge or a half-Wheatstone bridge.

13. Magnetoresistive sensor device according to claim 1, wherein the first and second magnetoresistive sensing elements are biased in a common direction.

14. Magnetoresistive sensor device according to claim 1, wherein each magnetoresistive sensing element comprises a strip of magnetoresistive material, the magnetoresistive material having a linear resistance versus magnetic field curve and being free of hysteresis.

15. Magnetoresistive sensor device according to claim 14, wherein a width of each of the first and second magnetoresistive sensing elements is at least 60% of the width of the probe element.

16. Magnetoresistive sensor device according to claim 14, wherein a width of each of the first and second magnetoresistive sensing elements is at least 70% of the width of the probe element.

17. Magnetoresistive sensor device according to claim 1, further comprising an additional electronic circuit arranged at least partially in the substrate and integrated with the comparator circuit.

18. Magnetoresistive sensor device according to claim 1, wherein a width of each of the first and second magnetoresistive sensing elements is at least 50% of the width of the probe element.

19. Magnetoresistive sensor device according to claim 1, wherein a distance of each of the first and second magnetoresistive sensing elements to the probe element is smaller than a width of the first and second magnetoresistive sensing elements.

20. Magnetoresistive sensor device according to claim 1, wherein the magnetic nanoparticles are superparamagnetic.

21. Magnetoresistive sensor device according to claim 1, wherein the substrate defines a probe area in which the probe element is arranged, the probe area having a profiled surface whereby parts of the profiled surface are at a different distance from the first and second magnetoresistive sensing elements as other parts of the profiled surface.

22. Magnetoresistive sensor device according to claim 21, wherein the profiled surface has a step profile.

23. Magnetoresistive sensor device according to claim 21, wherein the profiled surface has a gradient profile.

24. Magnetoresistive sensor according to claim 21, wherein the profiled surface is a chemically structured surface.

25. Magnetoresistive sensor according to claim 24, wherein the chemically structured surface is obtained by having binding sites on only part of the surface.

26. A system comprising the magnetoresistive sensor devise as claimed in claim 1, wherein the system is a blood tester.

27. Magnetoresistive sensor device according to claim 1, wherein width and length dimensions of the first and second magnetoresistive sensing elements are at least a factor of 100 or more larger than the average diameter of the nanoparticles.

28. Magnetoresistive sensor device according to claim 1, wherein the magnetoresistive sensor consists of only a single pair of first and second magnetoresistive sensing elements.

29. Magnetoresistive sensor device according to claim 1, wherein the magnetoresistive sensor comprises a plurality of pairs of first and second magnetoresistive sensing elements, the first magnetoresistive sensing element of all of the pairs being arranged under the first end region of the probe element and the second magnetoresistive element of all of the pairs being arranged under the second end region of the probe element.

30. Magnetoresistive sensor device according to claim 29, wherein the comparator circuit compares an output from a group of all of the first magnetoresistive sensing elements to an output from a group of all of the second magnetoresistive sensing elements.

31. Magnetoresistive sensor device according to claim 1, further comprising at least one additional probe element and at least one additional magnetoresistive sensor each arranged in association with a respective one of the at least one additional probe element, each of the at least one additional magnetoresistive sensor having the same features as the magnetoresistive sensor.

32. Magnetoresistive sensor device according to claim 1, wherein the first and second magnetoresistive elements are integrated into the substrate.

33. Magnetoresistive sensor device according to claim 1, wherein the first and second magnetoresistive sensing elements are spaced apart from one another such that the probe element overlies a space defined between the first and second magnetoresistive sensing elements.

34. A magnetoresistive sensor device for determining presence or an areal density of magnetic nanoparticles being coupled to a target, the magnetoresistive sensor device comprising:

a substrate defining a plurality of probe areas;

an elongate probe element arranged in each probe area on the substrate, each probe element including at least one binding site able to selectively bind a target, each probe element having first and second opposite end regions defining a length therebetween and extending in a first direction, and a magnetoresistive sensor arranged in association with each probe element for detecting a magnetic field of magnetic nanoparticles at least when coupled to the target bound to the at least one binding site of the associated probe element, each magnetoresistive sensor comprising at least one pair of discrete, elongate first and second magnetoresistive sensing elements each arranged only partially under the associated probe element, the first and second magnetoresistive elements each having a length and extending in the first direction such that the first and second magnetoresistive elements are parallel to the associated probe element, the first magnetoresistive element being arranged under the first end region of the associated probe element and the second magnetoresistive element being arranged under the second end region of the associated probe element such that the first and second magnetoresistive elements are separated and spaced apart from one another in the first direction, whereby outputs of the first, and second magnetoresistive elements are fed to a comparator circuit which determines the presence or the areal density of magnetic nanoparticles coupled to the target bound to the at least one binding site of the associated probe element.

35. Magnetoresistive sensor device according to claim 34, wherein the first and second magnetoresistive sensing elements of each magnetoresistive sensor device are arranged such that the probe area of the associated probe element only partially overlaps with the first and second magnetoresistive sensing elements.

* * * * *